(12) United States Patent
Keltgen

(10) Patent No.: US 8,388,341 B2
(45) Date of Patent: Mar. 5, 2013

(54) METHOD AND APPARATUS FOR ORGANIZING ORTHODONTIC SPACERS

(76) Inventor: Regina L. Keltgen, Elgin, TX (US)

( * ) Notice: Subject to any disclaimer, the term of this patent is extended or adjusted under 35 U.S.C. 154(b) by 0 days.

(21) Appl. No.: 13/174,053

(22) Filed: Jun. 30, 2011

(65) Prior Publication Data

US 2013/0004909 A1    Jan. 3, 2013

(51) Int. Cl.
*A61C 7/00* (2006.01)
(52) U.S. Cl. ............... 433/148; 433/3; 433/18
(58) Field of Classification Search ........... 433/2, 18, 433/148, 3; 221/33, 310; 206/63.5, 369, 206/388, 49, 227; 132/323, 324
See application file for complete search history.

(56) References Cited

U.S. PATENT DOCUMENTS

| | | | | |
|---|---|---|---|---|
| 4,217,099 A | * | 8/1980 | Thornton | 433/148 |
| 4,712,572 A | * | 12/1987 | Hovel, III | 132/321 |
| 4,807,752 A | * | 2/1989 | Chodorow | 206/63.5 |
| 2001/0049081 A1 | * | 12/2001 | Krupp | 433/18 |
| 2009/0215003 A1 | * | 8/2009 | Swain et al. | 433/24 |

\* cited by examiner

*Primary Examiner* — Cris L Rodriguez
*Assistant Examiner* — Eric Rosen
(74) *Attorney, Agent, or Firm* — Matthew E. Burr

(57) ABSTRACT

Orthodontic spacer and floss set-ups are organized on a set-up holder which is a thin square or rectangular piece of plastic that has a plurality of complementary notches formed across opposite sides. The spacer is positioned more or less in between the notches on the set-up holder and one length of floss is disposed in one notch while the other length of floss is disposed in the complementary notch on the opposite side of the holder. In a supply of two or more spacer set-ups, the set-ups are separated from each other in this manner so that a particular one does not have to be untangled from a jumble of other set-ups. Kits provide pre-made set-ups already organized on a piece of notched plastic.

12 Claims, 4 Drawing Sheets

US 8,388,341 B2

METHOD AND APPARATUS FOR ORGANIZING ORTHODONTIC SPACERS

TECHNICAL FIELD

This disclosure relates generally to orthodontic tools and more particularly to a method and apparatus for organizing orthodontic spacers.

BACKGROUND

Orthodontic separators are commonly known as spacers. Usually they are small rubber bands or metal appliances used in orthodontics. Often, spacers are placed between the molars during the orthodontic session in which a palatal expander or braces are to be fitted. Spacers are typically toroidal rubber bands about a centimeter in diameter placed between top and bottom molars. There may be anywhere from 1 to 12 spacers inserted for a given patient. The spacers stay between the teeth for one to two weeks and move the teeth apart slowly until they are far apart enough so that the orthodontist can fit a tooth brace in between them or fit an expander with metal rings.

For rubber band spacers, the standard method of inserting them between the teeth of a patient is to thread two lengths of dental floss through the rubber band, using the dental floss to stretch the rubber, placing the stretched rubber band between the teeth and working the rubber band down between the teeth with the floss. For the purposes of this disclosure, the arrangement of the pair of floss segments through the rubber band spacer will be referred to as a spacer "set-up." Of course floss is only a specific embodiment and it is understood that any thread of sufficient strength is suitable.

In a busy office, an orthodontist may have a dozen or more spacer set-ups with floss and rubber bands. It is not surprising that the spacer set-ups often become tangled or jumbled. The floss and even the rubber bands can get mixed up with other tools or equipment on a tray. It can be tedious and annoying to untangle the set-ups, to keep them organized and contained so that they cannot cause trouble.

There is a need therefore, for a method and apparatus to organize orthodontic spacer set-ups.

SUMMARY

Spacer and floss set-ups are organized on relatively thin set-up holder also called a "slab") made of, for example, plastic or polyurethane. In specific embodiments, the set-up holder is a square or rectangular piece of plastic that has plurality of complimentary notches formed across opposite sides. The spacer is positioned more or less midway between the sides of the slab and one length of floss extends from the spacer and is disposed in one notch while the other length of floss extends from the spacer and is disposed in the complimentary notch on the opposite side of the slab. Accordingly, a plurality of set-ups can be organized on one slab such that, by being secured in the notches of the slab, the lengths of floss are substantially prevented from becoming entangled together or entangled in orthodontic equipment. In a supply of two or more set-ups, the set-ups are separated from each other in this manner so that a particular one does not have to be untangled from a jumble of other set-ups. Kits are contemplated wherein pre-made set-ups are provided already organized on a set-up holder.

BRIEF DESCRIPTION OF THE DRAWINGS

For a more complete understanding of the present disclosure, and the advantages thereof, reference is now made to the following descriptions taken in conjunction with the accompanying drawings, in which.

DETAILED DESCRIPTION

Figure 1:
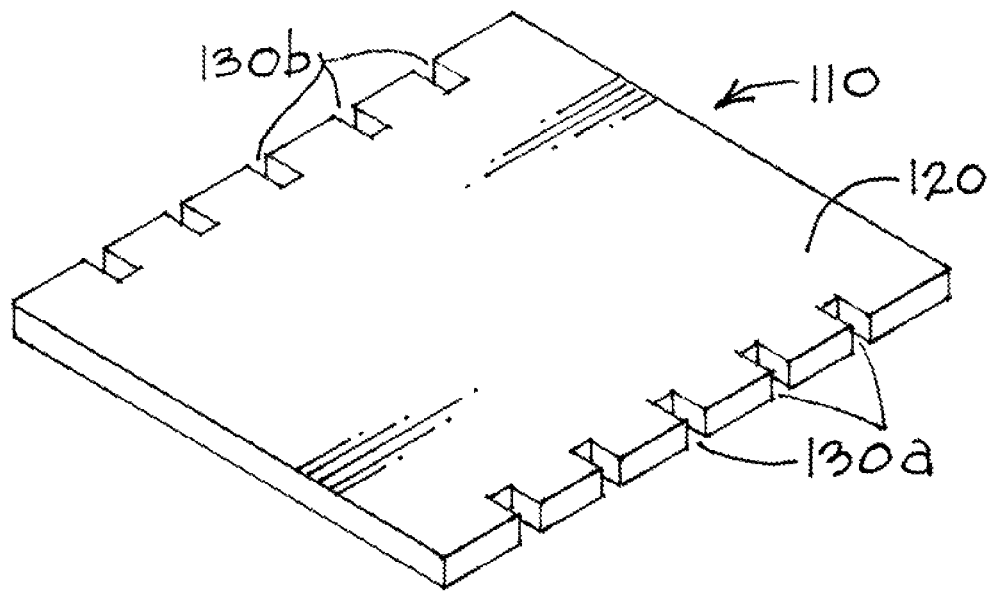
FIG. 1 is a top view isometric perspective illustration of a set-up holder piece of an exemplary embodiment of an orthodontic tool of the present disclosure.

In general, a tool of the present disclosure provides a substantially planar slab piece, or set-up holder, on which spacer and floss set-ups are organized. As used herein, the set-up holder pieces are referred to from time to time as a "slab" or "slab piece."

In specific embodiments, the set-up holder is a square or rectangular piece of plastic or other suitable material that has plurality of complimentary notches formed across opposite sides. The spacer is positioned more or less in the center of the slab and one length of floss is disposed in one notch while the other length of floss is disposed in the complimentary notch on the opposite side of the slab. Accordingly, a plurality of set-ups can be organized on one slab such that lengths of floss are substantially prevented from becoming entangled together or in orthodontic equipment by being secured in the notches of the slab set-up holder. In a supply of two or more set-ups, the set-ups are separated from each other in this manner so that a particular one does not have to be untangled from a jumble of other set-ups. Furthermore, kits are contemplated wherein pre-made set-ups are provided already organized on a slab.

It will be clear from the disclosure that the precise material or materials from which the set-up holder piece is manufactured, and the shape of the set-up holder piece, is a matter of engineering design choice. In some applications of the present tool, a durable, reusable, set-up holder piece may be advantageous, and therefore a polyurethane, polyester, or other type of plastic material would be suitable. On the other hand, there may be circumstances under which a disposable or inexpensive tool may be advantageous and therefore slabs made from cardboard or the like would be suitable. Additional suitable materials include, but are not limited to, recycled materials, wood, glass, composites, and so forth. Rubber or other pliable materials are also suitable for particular embodiments. So long as the material provides sufficient rigidity to achieve the organization of the spacer/floss set-ups, the material will in all likelihood be suitable for use in one or more orthodontic settings.

A further consideration is that, preferably, the material the set-up holder is fabricated from well tolerates sterilization solutions or measures so that the holder can be sterilized for reuse. Indeed, the set-up holder, at least, is preferably sterilizable so that the holders can be sterilized prior to use with a patient. Typically the set-up holder piece is cold sterilized in glutaraldehyde, but the present disclosure contemplates alternative embodiments that tolerate autoclave sterilization.

Decorative slab pieces are contemplated. For example, slabs may display the logo of a sports team or school. Decorative pieces include, without limitation, promotional displays such as orthodontic equipment advertisements and the like. In addition to information displays such as logos or advertising, the slab pieces may be manufactured in a variety of decorative shapes and in various colors and color combinations.

Turning now to the drawings and referring to FIG. 1, FIG. 1 is a top view isometric perspective illustration of a slab piece of an exemplary embodiment of an orthodontic tool of the present disclosure. Reference numeral 110 generally designates a slab piece embodying features of the present disclosure. Set-up holder piece 110 provides a substantially planar structure, in this example it is generally rectangular in shape, having a body portion 120 and a plurality of perimeter notches 130a along at least one side. A set of complimentary notches 130b is provided on the side opposite set 130a. That is, slab piece 110 provides complimentary opposed perimeter notches. Specific alternative embodiments (not shown) provide complimentary notches around the entire perimeter of the set-up holder piece. In such alternative embodiments the set-ups may be disposed on the set-up holder in a cross-hatching typo arrangement.

Figure 2:
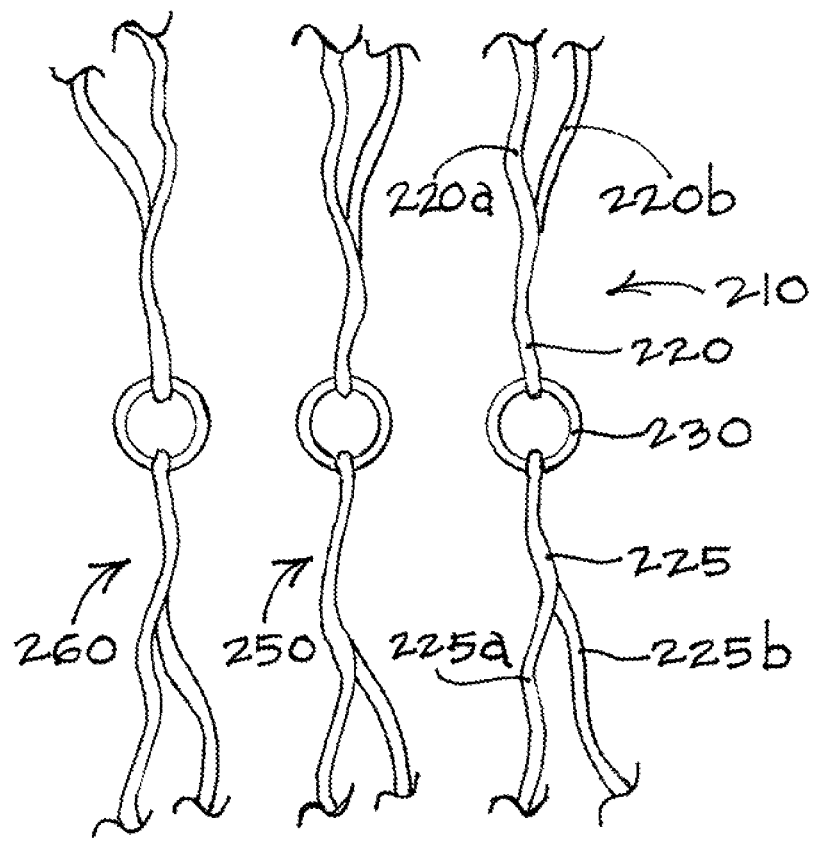
FIG. 2 is a top view illustration of a set of spacer/floss set-ups of an orthodontic tool of the present disclosure.

FIG. 2 is a top view illustration of a set of spacer/floss set-ups of an orthodontic tool of the present disclosure. Set-ups 210, 250, and 260 are functionally equivalent. Describing set-up 210 as an example, spacer 230 is typically a rubber band-type elastic torus, through the hole of which are laced a pair of threads 220,225, usually of dental floss. By virtue of being laced through toroidal spacer 230, threads 220 and 225 form paired strands, 220a, 220b and 225a, 225b, respectively. In operation, threads 220,225 spacer 230 are pulled and stretched spacer 230 so the rubber becomes thinner. In this thinner state, the rubber is more easily inserted in between teeth. After insertion between teeth, the rubber is allowed to relax by release and removal of the threads 220,225. In a relax state, the rubber of spacer 230 becomes thicker and puts pressure on the teeth it is between to spread the teeth apart.

Figure 3:
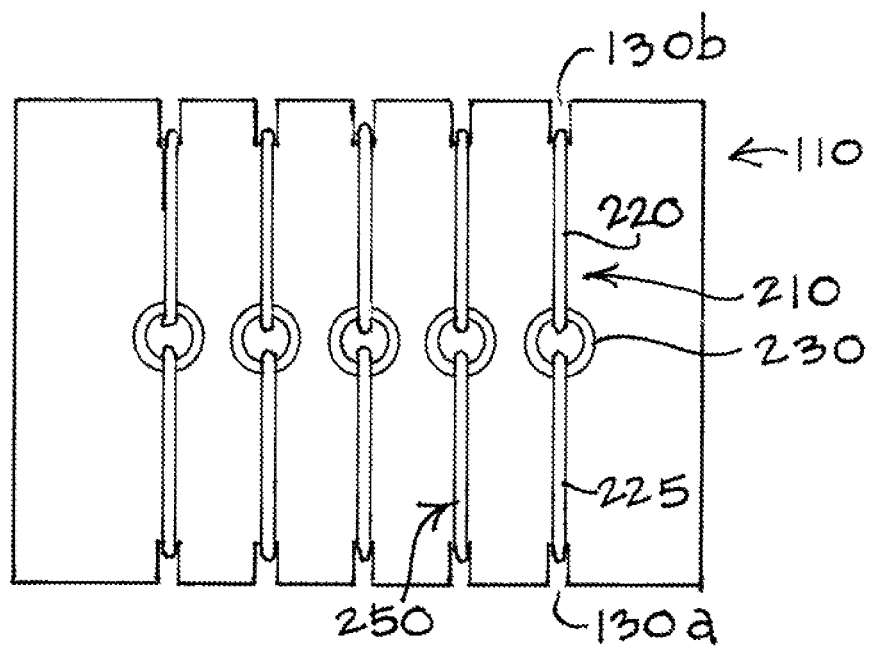
FIG. 3 is a top view illustration of an exemplary embodiment of an orthodontic tool of the present disclosure.

FIG. 3 is a top view illustration of an exemplary embodiment of an orthodontic tool of the present disclosure. Set-ups are arranged on the slab piece with the spacer 230 more or less midway between the notches on the slab. Floss threads 225, 220 wrap around slab 110 and are disposed in complimentary notches 130a, 130b, respectively, to retain the threads in a relatively confined position. Preferably, the surface texture in notches 130a, 130b is smooth and the notches are sufficiently thin to retain the set-up threads by snug friction fit. Also, waxed floss is the preferred type of thread for the set-ups because the wax helps retain the thread in the notch. It will be understood that the illustrations of the notches in this disclosure are not necessarily to scale and show the notch size somewhat exaggerated for illustrative purposes.

Figure 4:
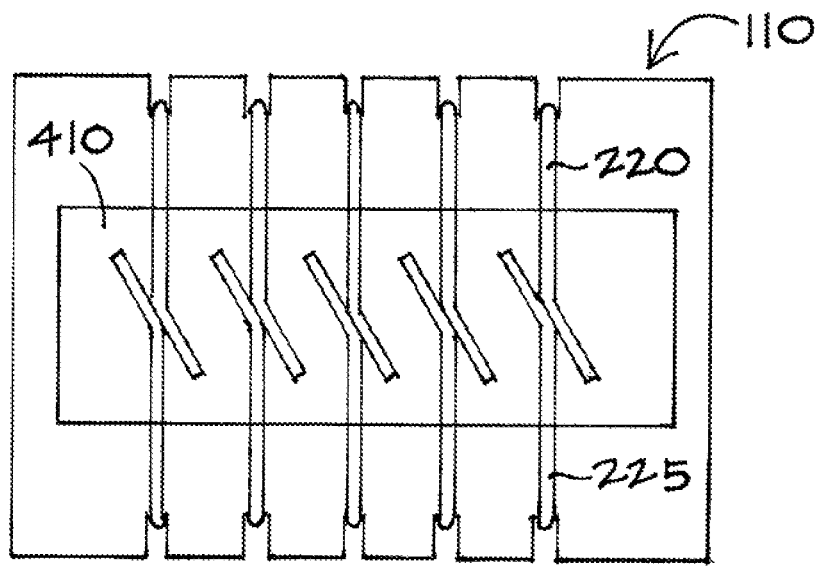
FIG. 4 is a bottom view illustration of the orthodontic tool of FIG. 3.

FIG. 4 is a bottom view illustration of an orthodontic tool of the present disclosure. Floss threads 220, 225 are secured in place with adhesive strip 410. The embodiment of this FIG. 4 is particularly advantageous for kits in which pre-made set-ups are provided.

Figure 5:
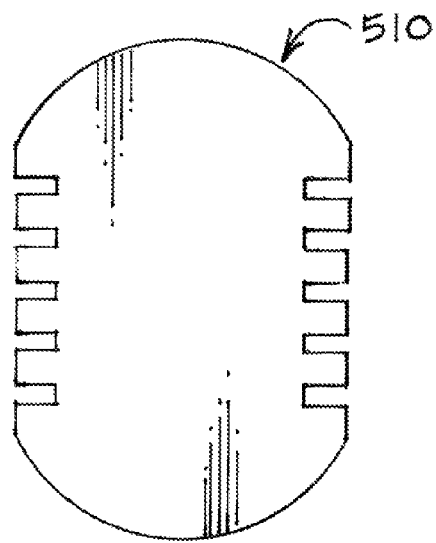
FIG. 5 is a top view illustration of an exemplary alternative embodiment of a set-up holder piece of an orthodontic tool of the present disclosure.
Figure 6:
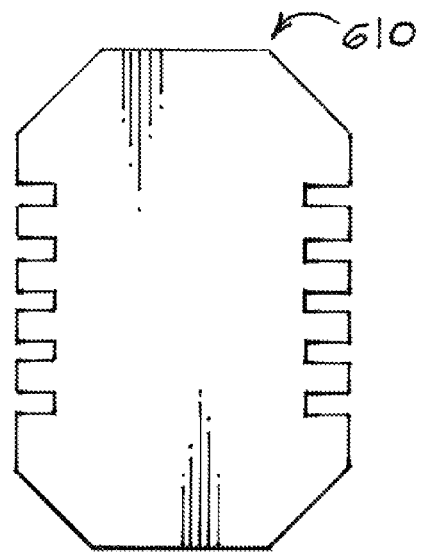
FIG. 6 is a top view illustration of another exemplary alternative embodiment of a set-up holder piece of an orthodontic tool of the present disclosure.
Figure 7:
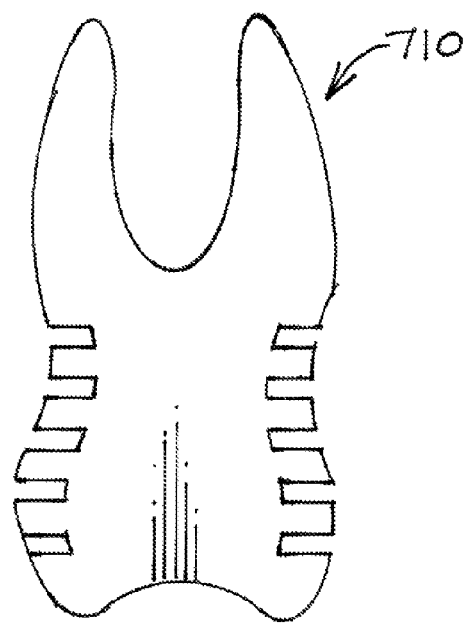
FIG. 7 is a top view illustration of a further exemplary alternative embodiment of a set-up holder piece of an orthodontic tool of the present disclosure.
Figure 8:
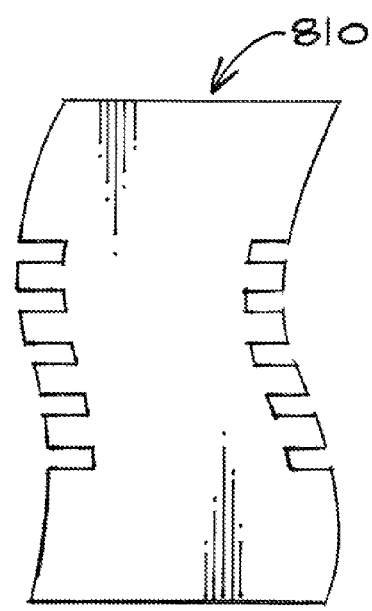
FIG. 8 is a top view illustration of yet another exemplary alternative embodiment of a slab piece of an orthodontic tool of the present disclosure.

FIGS. 5-8 depict various exemplary shape embodiments of a slab piece of the present tool. FIG. 5 shows an embodiment 510 having curved ends. FIG. 6 shows an embodiment 610 having an extended octagonal shape. FIG. 7 shows a decorative embodiment 710 that suggests the shape of a tooth. FIG. 8 shows an embodiment 810 having a curvilinear wave form.

Figure 9:
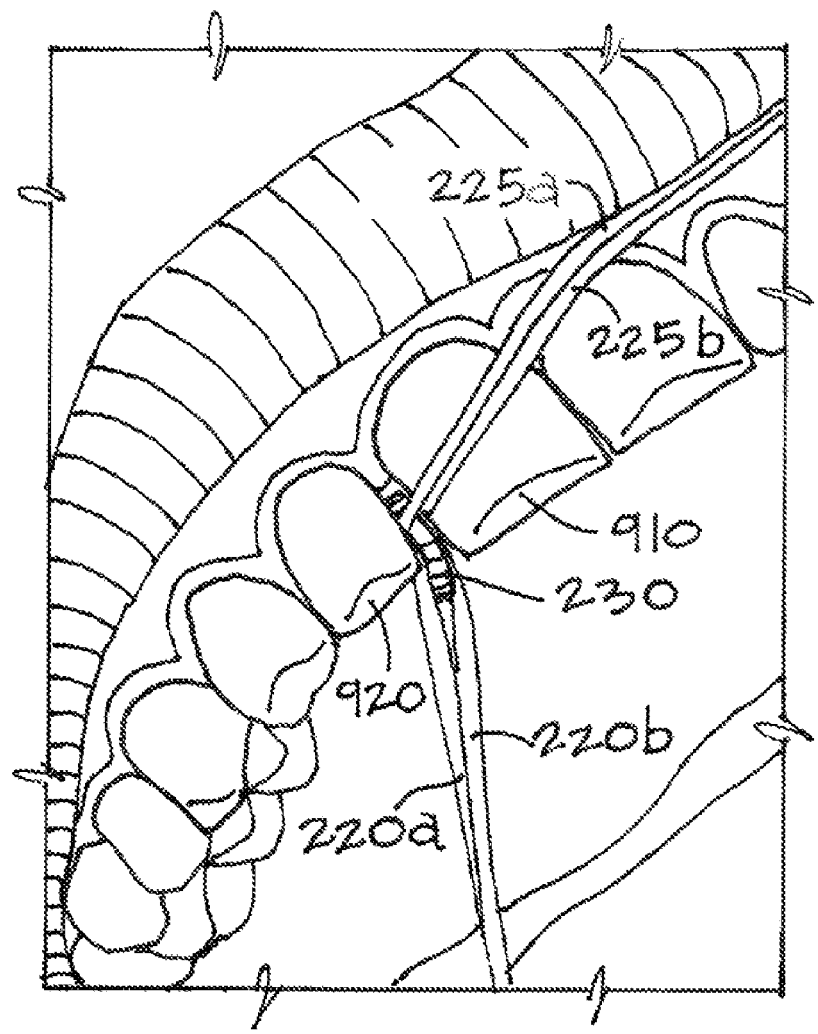
FIG. 9 is front view isometric perspective illustration of a spacer being inserted between teeth with a spacer/floss set-up.

FIG. 9 is front view isometric perspective illustration of a spacer being inserted between teeth with a spacer/floss set-up. Spacer 230 is inserted between teeth 910, 920 with floss segments 225a,225b and 220a,220b. The floss segments are used to stretch the rubber spacer so that the rubber becomes thin enough the work between the teeth. Once the spacer is position as desired, the floss segments are removed from the spacer and the spacer remains positioned between the teeth. When the spacer is not stretched, the rubber thickens and pushes the teeth apart slowly. Orthodontia often entails placing more than one spacer in a patient's mouth to straighten teeth or to prepare teeth for braces or other orthodontic appliances.

The use of a spacer set-up organizing tool of the present disclosure provides significant advantages over the prior art. Set-ups organized on a set-up holder reduce aggravation caused by tangled loose set-ups and produce a more professional work environment for orthodontic clinics.

The present disclosure contemplates kits of set-ups and set-up holders. Specific embodiments of a kit for organizing orthodontic spacers consist of a plurality of orthodontic spacer set-ups, each set-up consisting of one toroidal-shaped elastic spacer having two pieces of thread disposed through the hole of the toroidal spacer. The set-ups are packaged with one or more set-up holders. Each holder has at least one pair of opposing sides with one or more pairs of complimentary notches such that a first side of the holder has at least one notch and the opposite side has at least one complimentary notch. Each kit comes with a set of instructions which explains how to organize the spacer set-ups on each set-up holder. Alternative embodiments provide the instructions online via a website that can be accessed by a networked device that can display a web browser.

Alternative embodiments provide one or more kits that include without limitation one or more set-ups pre-organized on one or more set-up holders, as depicted in FIGS. 3 and 4.

Methods for organizing orthodontic spacer set-ups include without limitation steps for (1) providing one or more orthodontic spacer set-ups, where each set-up consists of one toroidal-shaped elastic spacer having two pieces of thread disposed through the hole of the toroidal spacer; (2) providing a set-up holder having at least one pair of opposing sides, the holder comprising one or more pair of complimentary notches such that a first side of the holder has at least one notch and the opposite side has at least one complimentary notch; and (3) arranging of at least one set-up on the holder such that the spacer rests on the holder and each piece of thread is disposed in a respective holder notch.

Many modifications and other embodiments of the spacer/floss set-up organizing tool described herein will come to mind to one skilled in the art to which this disclosure pertains having the benefit of the teachings presented in the foregoing descriptions and the associated drawings. Therefore, is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An orthodontic tool for providing orthodontic spacer set-ups, the tool comprising:
   a. one or more orthodontic spacer set-ups, each of the one or more set-ups consisting of one toroidal-shaped elastic spacer having two unconnected pieces of thread disposed through the hole of the toroidal spacer;
   b. a set-up holder having at least one pair of opposing sides, the holder comprising one or more pairs of complimentary notches such that a first side of the holder has at least one notch and a second side has at least one complimentary notch;
      wherein at least one of the one or more set-ups is arranged on the set-up holder such that the spacer of each of the at least one of the one or more set-ups rests on the holder and the two pieces of thread of each of the at least one of the one or more set-ups is disposed in a respective one of the notches.

2. The tool of claim 1, wherein the holder comprises plastic.

3. The tool of claim 1, wherein the holder tolerates sterilization.

4. The tool of claim 1, wherein the holder comprises a non-quadrilateral shape.

5. The tool of claim 1, wherein the holder displays information.

6. The tool of claim 1, comprising a plurality of the one or more spacer set-ups arranged on the holder.

7. The tool of claim 1, wherein at least one of the two threads of one of the one or more spacer set-ups comprises a length of dental floss.

8. The tool of claim 1, wherein at least one spacer of the one or more spacer set-ups comprises rubber.

9. A kit for organizing orthodontic spacers, the kit comprising:
   a. A plurality of orthodontic spacer set-ups, each of the plurality of set-ups consisting of one toroidal-shaped elastic spacer having two unconnected pieces of thread disposed through the hole of the toroidal spacer;
   b. one or more set-up holders packaged with the spacer set-ups, each holder having at least one pair of opposing sides, each holder comprising one or more pairs of complimentary notches such that a first side of each holder has at least one notch and a second side of each holder, opposite the first side, has at least one complimentary notch.

10. The kit of claim 9, wherein one or more of the plurality of set-ups are pre-organized on at least one of the one or more set-up holders.

11. The kit of claim 9, further comprising instructions that explain how to organize the spacer set-ups on each of the one or more set-up holders.

12. A method for organizing orthodontic spacer set-ups, the method comprising:
   a. providing one or more orthodontic spacer set-ups, each of the one or more set-ups consisting of one toroidal-shaped elastic spacer having two unconnected pieces of thread disposed through the hole of the toroidal spacer;
   b. providing a set-up holder having at least one pair of opposing sides, the holder comprising one or more pairs of complimentary notches such that a first side of the holder has at least one notch and a second side, opposite the first side, has at least one complimentary notch; and
   c. arranging at least one of the one or more set-ups on the set-up holder such that the spacer of each of the at least one of the one or more set-ups rests on the holder and the two pieces of thread of each of the at least one of the one or more set-ups is disposed in one of the notches.

* * * * *